United States Patent [19]

Arison et al.

[11] Patent Number: 5,124,258

[45] Date of Patent: Jun. 23, 1992

[54] FERMENTATION PROCESS FOR THE PREPARATION OF IVERMECTIN AGLYCONE

[75] Inventors: Byron H. Arison, Watchung; Patrick J. Doherty, Edison; Marvin D. Schulman, Scotch Plains, all of N.J.

[73] Assignee: Merck & Co., Inc., Rahway, N.J.

[21] Appl. No.: 580,999

[22] Filed: Sep. 12, 1990

[51] Int. Cl.$^5$ .................. C12P 17/18; C12P 17/16; C12R 1/01
[52] U.S. Cl. .................. 435/119; 435/75; 435/76; 435/118; 435/822
[58] Field of Search .................. 435/119, 75–76, 435/822, 118

[56] References Cited

U.S. PATENT DOCUMENTS 4,206,205  6/1980  Mrozik et al. .................. 536/7.1
4,895,837  1/1990  Mrozik et al. .................. 536/7.1

OTHER PUBLICATIONS

Biotech Abs 90-00736 (ACSRAL) Pap. Am Chem Soc (1989) 198 Meeting Abs. MBTD 134 (Abs) Paulus et al.

*Primary Examiner*—Herbert J. Lilling
*Attorney, Agent, or Firm*—David L. Rose; Joseph F. DiPrima

[57] ABSTRACT

Fermentation of *S. erythraea* produces the novel avermectin, 28-hydroxy ivermectin aglycone.

2 Claims, 1 Drawing Sheet

FERMENTATION PROCESS FOR THE PREPARATION OF IVERMECTIN AGLYCONE

BACKGROUND OF THE INVENTION

The preparation of ivermectin aglycone is known and is described, for instance, in U.S. Pat. No. 4,206,205. Derivatives of ivermectin aglycone that are hydroxylated in the 28-position, however, have not previously been disclosed.

OBJECTS OF THE INVENTION

It is, accordingly, an object of the present invention to provide the 28-hydroxy derivative of ivermectin aglycone. Another object is to provide a method for the preparation of 28-hydroxy ivermectin aglycone. A further object is to provide various fermentation media that are suitable for the preparation of 28-hydroxy ivermectin aglycone. A still further object is to provide methods and formulations for using this compound. These and other objects of the present invention will be apparent from the following description.

SUMMARY OF THE INVENTION

Ivermectin aglycone is added to a complex nutrient fermentation media of Saccharopolyspora erythraea, and the fermentation is continued until a desired quantity of 28-hydroxy aglycone is achieved.

DETAILED DESCRIPTION

Figure 1:
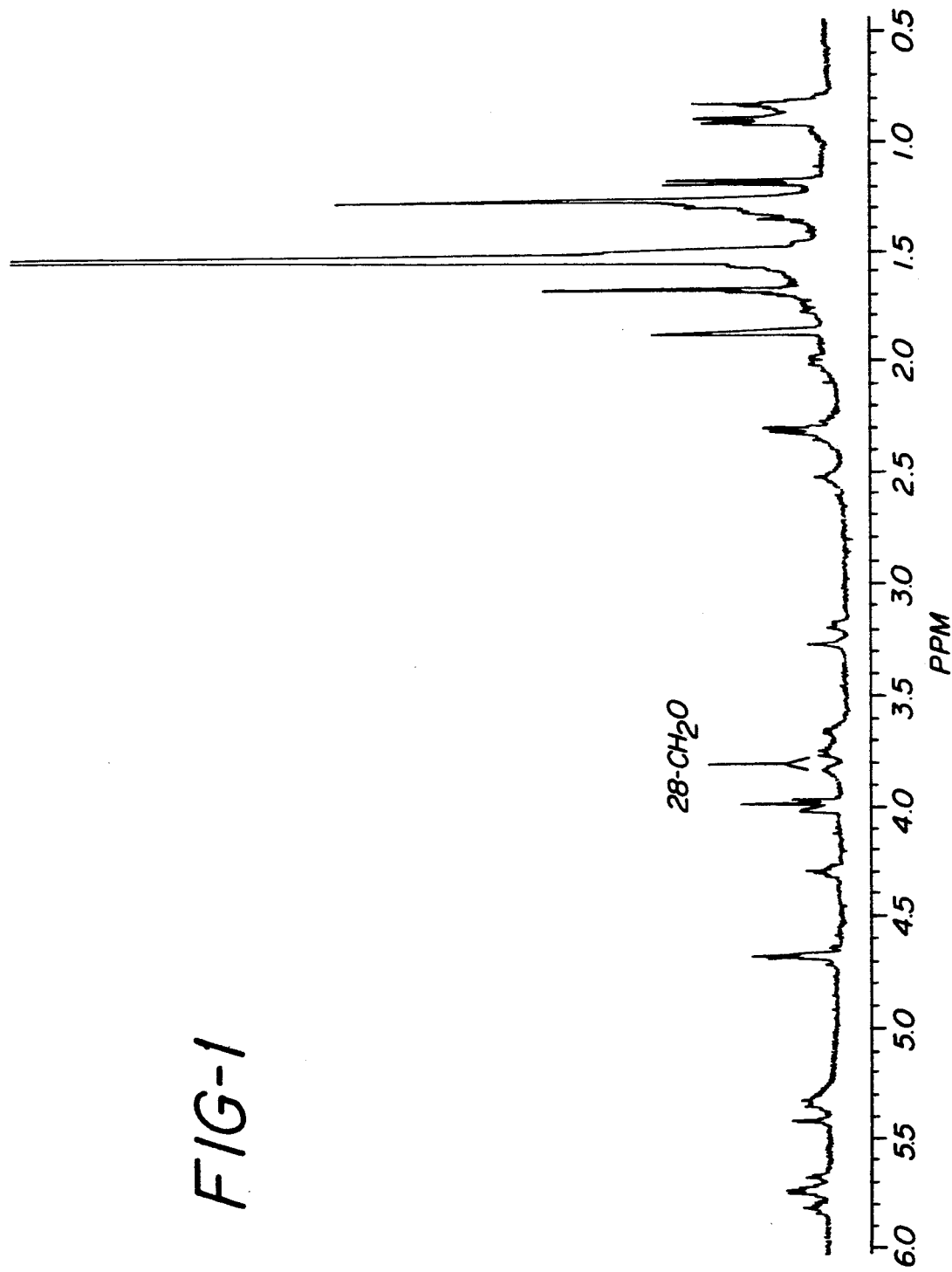
FIG. 1 shows the NMR spectrum of 28-hydroxy ivermectin aglycone.

The present invention is concerned with the preparation of 28-hydroxy ivermectin aglycone by adding to a fermentation medium of Saccharopolyspora erythraea a quantity of ivermectin aglycone. S. erythraea is a known organism and culture deposits are available, for instance, from American Type Culture Collection. While the present invention is exemplified with S. erythraea strain ATCC 11635, it is to be understood that other strains of this organism, and mutants that are obtained by natural by mutating agents such as, for example, x-ray irradiation, ultraviolet radiation, nitrogen mustard or like treatments are also included within the scope of this invention.

The fermentation is carried out in a medium containing S. erythraea and results in the production of 28-hydroxy aglycone having the formula

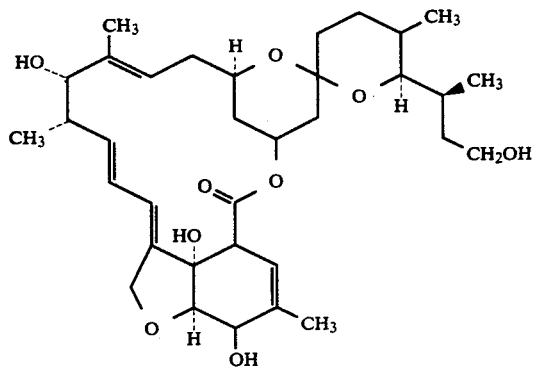

The instant compound is produced during the aerobic fermentation of suitable aqueous nutrient media under conditions described hereinafter, with a producing strain of S. erythraea. Aqueous media such as those used for the production of many antibiotic substances are suitable for use in the process for the production of this macrocyclic compound.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example glucose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by S. erythraea, in the production of the instant compounds. The various sources of nitrogen can be used alone or in combination in amounts ranging from 1 to 5 g/l in the medium.

Among the nutrient inorganic salts which can be incorporated in the culture media are the customary salts capable of yielding sodium, potassium, magnesium, ammonium, calcium, phosphate, sulfate, chloride, carbonate, and like ions. Also included are trace metals such as iron, zinc, manganese, copper, boron, molybdenum and the like.

It should be noted that the media described hereinbelow and in the Examples are merely illustrative of the wide variety of media, which may be employed, and are not intended to be limiting.

The following are examples of media suitable for growing strains of Saccharopolyspora erythraea ATCC 11635:

| MEDIUM 1 | |
|---|---|
| Glucose | 50 g |
| NaCl | 5 g |
| (NH$_4$)$_2$SO$_4$ | 2 g |
| CaCO$_3$ | 6 g |
| Soya Flour Extract | 30 g |
| Distilled Water | 1000 ml |
| Adjust pH to 7.0 | |
| MEDIUM 2 | |
| Dextrose | 20 g |
| Peptone | 5 g |
| Meat Extract | 5 g |
| Primary Yeast | 3 g |
| NaCl | 5 g |
| CaCO$_3$ | 3 g |
| Distilled Water | 1000 ml |
| Adjust pH to 7.0 | |
| MEDIUM 3 | |
| Soluble Starch | 10 g |

-continued

| | |
|---|---|
| Ardamine pH | 5 g |
| NZ amine E | 5 g |
| Beef Extract | 3 g |
| MgSO$_4$.7H$_2$O | 0.5 g |
| Cerelose | 1.0 g |
| Na$_2$HPO$_4$ | 0.190 g |
| KH$_2$PO$_4$ | 0.182 g |
| CaCO$_3$ | 0.05 g |
| Distilled Water | 1000 ml |
| MEDIUM 4 | |
| Cerelose | 10 g |
| Corn Starch | 40 g |
| Glycine | 7.5 g |
| Tyrosine | 0.9 g |
| Triolein | 2.5 g |
| NaCl | 2.0 g |
| K$_2$HPO$_4$ | 1.56 g |
| KH$_2$PO$_4$ | 0.78 g |
| MgSO$_4$.7H$_2$O | 0.5 g |
| CoCl$_2$.6H$_2$O | 0.001 g |
| FeSO$_4$.7H$_2$O | 0.02 g |
| MnCl$_2$.4H$_2$O | 0.001 g |
| ZnSO$_4$.7H$_2$O | 0.05 g |
| CaCO$_3$ | 3.0 g |
| Distilled Water | 1000 ml |
| MEDIUM 5 (SLANT) | |
| Yeast Extract | 4 g |
| Malt Extract | 10 g |
| Dextrose | 4 g |
| Bacto Agar | 20 g |
| Distilled Water | 1000 ml |
| pH 7.0 | |
| MEDIUM 6 | |
| Cerelose | 15 g |
| Soybean meal | 15 g |
| CaCO$_3$ | 1.0 g |
| Distilled Water | 1000 ml |
| Adjust pH to 7.0-7.2 | |

The fermentation employing S. erythraea can be conducted at temperatures ranging from about 20° C. to about 40° C. For optimum results, it is most convenient to conduct these fermentations at a temperature in the range of from about 24° C. to about 36° C. Temperatures of from about 28° C. to about 34° C. are most preferred. The pH of the nutrient medium suitable for producing the instant compounds can vary from about 6.5 to about 8.0 with a preferred range of from about 6.8 to about 7.3.

The ivermectin aglycone starting compound is added to the fermentation of S. erythraea in quantities of from about 0.1 to about 1.0 g per liter of fermentation medium. It is preferred to use from about 0.1 to about 0.5 g per liter. The ivermectin aglycone compound may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the ivermectin aglycone starting compound be added to the fermentation before 50% of the cycle is completed, preferably before 25% of the cycle is completed.

Small scale fermentations are conveniently carried out by placing suitable quantities of nutrient medium in a flask employing known sterile techniques, inoculating the flask with either spores or vegetative cellular growth of S. erythraea, loosely stoppering the flask with cotton and permitting the fermentation to proceed in a constant room temperature of about 30° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of S. erythraea. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (LPM) of air.

The separation of the novel compound from the whole fermentation broth and the recovery of the compound is carried out by solvent extraction and application of chromatographic fractionations with various chromatographic techniques and solvent systems.

The instant compound has slight solubility in water, but is soluble in organic solvents. This property conveniently may be employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column preferably containing silica gel. The column retains the desired product and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as others known to those skilled in the art, will afford purified compositions containing the instant compound. The presence of the desired compound is determined by analyzing the various chromatographic fractions for biological activity of physico-chemical characteristics. The structures of the instant compound has been determined by detailed analysis of the various spectral characteristics of the compounds, in particular their nuclear magnetic resonance, mass, ultraviolet and infrared spectra.

The compound of this invention has significant parasiticidal activity as an anthelmintic, an insecticide and an acaricide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Stongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compound is also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra intestinal stages of the intestinal worms Strongyloides and Trichinella. The compound is also of value against arthropods parasitizing man, biting insects and other dipterous pests causing annoyance to man.

The instant compound is also active against household pests such as the cockroach, Blatella sp., clothes moth, Tineola sp., carpet beetle, Attagenus sp. and the housefly *Musca domestica.*

The compound of the present invention is also useful against insect pests of stored grains such as Tribolium sp., Tenebrio sp. and of agricultural plants such as spider mites, (Tetranychus sp.), aphids, Acyrthiosiphon migratory orthopterans such as locusts and immature stages of insects living on plant tissue. The compound is useful as a nematocide for the control of soil nematodes and plant parasites such as Meloidogyne spp. which may be of importance in agriculture.

The instant compound can be administered orally in a unit dosage form such as a capsule, bolus or tablet, or as a liquid drench that is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to about 0.5% by weight of the active compound. Preferred drench formulations may contain from about 0.01 to about 0.1% by weight. The capsules and boluses comprise the active ingredient admixed with a carrier vehicle such as starch, talc, magnesium stearate, or dicalcium phosphate.

Where it is desired to administer the compound of the present invention in a dry, solid unit dosage form, capsules, boluses or tablets containing the desired amount of the instant compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the compound of the present invention is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The compound of the present invention is dissolved or suspended in the parenteral formulation for administration; such formulations generally contain from about 0.55% to about 5% by weight of the instant compound.

Although the compound of this invention finds its primary use as an antiparasitic agent in the treatment and/or prevention and treatment of diseases caused by parasites, for example, arthropod parasites such as ticks, lice, fleas, mites and other biting insects in domesticated animals and poultry, they are also effective in treatment of parasitic diseases that occur in other animals including humans. The optimum amount to be employed for best results will, of course, depend upon the species of animal to be treated and the type and severity of parasitic infection or infestation. Generally, good results are obtained with our novel compound by the oral administration of from about 0.001 to about 10 mg per kg of animal body weight, such total dose being given at one time or in divided doses over a relatively short period of time such as 1-5 days. With the novel compound of the present invention, excellent control of such parasites is obtained in animals by administering from about 0.025 to about 0.5 mg per kg of body weight in a single dose. Repeat treatments are given where required to combat re-infections and are dependent upon the species of parasite and the husbandry techniques being employed. The techniques for administering these materials to animals are known to those skilled in the veterinary field.

When the compound described herein is administered as a component of the feed of the animals, or dissolved or suspended in the drinking water, compositions are provided in which the active compound is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the instant compound is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The compound of the present invention is intimately dispersed throughout the carrier by methods such as grinding, stirring, milling or tumbling. Compositions containing from about 0.005% to about 2.0% by weight of the instant compound are particularly suitable as feed premixes. Feed supplements, which are fed directly to the animal, contain from about 0.0002% to about 0.3% by weight of the instant compound.

Such supplements are added to the animal feed in an amount to give the finished feed the concentration of active compound desired for the treatment and control of parasitic diseases. Although the desired concentration of the compound of the present invention will vary depending upon the factors previously mentioned as well as upon the particular compound employed, the compound of this invention is usually fed at concentrations of between about 0.00001% to about 0.002% in the feed in order to achieve the desired antiparasitic result.

In addition, where the compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compound of this invention also is useful in combatting agricultural pests that inflict damage upon crops while they are growing or while in storage. The compound is applied using known techniques as sprays, dusts, emulsions and the like, to the growing or stored crops to effect protection from such agricultural pests.

The anthelmintic activity of the instant compound may be determined by orally administering via the feed, a sample of the individual compound, a mixture of such compound, a concentrated extract, and the like to a mouse which had been infected 3 days earlier with a gastrointestinal parasite. At 11, 12 and 13 days after the initiation of the medication, the feces of the mouse are examined for eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

*S. erythraea* (ATCC 11635) was grown in medium M102 as described by Corcoran (Methods in Enzymology 43: 487-498 1975). It contained the following in 1000 ml of distilled water: glucose, 5 g; commercial brown sugar (Domino's), 10 g; tryptone, 5 g; yeast extract, 2.5 g; ethylene diamine tetraacetate, 0.036 g; betaine, 1.2 g; sodium propionate, 0.11 g. The medium was adjusted to pH 7.0-7.2 and 2.2 ml of trace elements solution which contained the following in g/l were added:

$FeCl_3 \cdot 6H_2O$, 0.2; $ZnCl_2$, 0.04; $MnCl_2 \cdot 4H_2O$, 0.01; $CuCl_2 \cdot 2H_2O$, 0.01; $NaB_4O_7 \cdot 10H_2O$, 0.01; $(NH_4)_6Mo_7O_{24} \cdot 4H_2O$, 0.01.

INOCULUM PREPARATION

Frozen vegetative mycelia (FVM) were prepared by inoculating 250 ml media in a 2 liter 3 baffle flask and incubating at 32° C., 85% relative humidity and 200 RPM for 48 hours. The packed cell volume of the culture was 10% and the pH 6.9. Aliquots of the culture were frozen and used as source of inoculum for future experiments.

SEED CULTURE

To 40 ml of medium M102 in a 250 ml flask, 1.0 ml of FVM was added as inoculum and the flasks were incubated at 30° C., 85% relative humidity and 200 RPM for 40 hours.

BIOTRANSFORMATION AND ISOLATION

To 40 ml of medium M102 in a 250 ml flask, 1.0 ml of seed culture was added and flasks were incubated at 30° C., 85% relative humidity at 200 RPM for 24 hours. 2.5 mg of ivermectin aglycone in 0.1 ml DMSO were added and the flasks were incubated as above for 5 days. Each flask was extracted with 2×80 ml portions of $CH_2Cl_2$. The $CH_2Cl_2$ extracts were combined, concentrated and the avermectins were partially purified by preparative TLC on silica gel 60 using methylene chloride:ethylacetate:methanol (9:9:1) as the solvent. The individual avermectin bands were eluted from the silica, concentrated and further purified by HPLC on Dupont Zorbax ODS using $CH_3OH:H_2O$ (80:20 or 70:30) as the mobile phase. The structures of the purified avermectins were determined by mass spectroscopy and NMR spectroscopy. The NMR spectrum was recorded in $CDCl_3$ at ambient temperature on a Varian UNITY 400 spectrometer. Chemical shifts are shown in ppm relative to internal tetramethylsilane at zero ppm.

What is claimed is:

1. A process for the preparation of a compound having the formula:

which comprises adding ivermectin aglycone to the fermentation medium of a species of the microorganism *Saccharopolyspora erythraea* that is effective to convert ivermectin aglycone into 28-hydroxy ivermectin aglycone.

2. The process of claim 1 wherein the S. erythraea microorganism is ATCC 11635.

* * * * *